United States Patent
Cavallo et al.

(12) 
(10) Patent No.: US 6,337,087 B1
(45) Date of Patent: Jan. 8, 2002

(54) AQUEOUS PHARMACEUTICAL COMPOSITION COMPRISING AN ACTIVE INGREDIENT WHICH IS HIGHLY INSOLUBLE IN WATER

(75) Inventors: Giovanni Cavallo, Ostia; Leonardo Marchitto, Cupra Marittima, both of (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 09/367,699
(22) PCT Filed: Feb. 12, 1998
(86) PCT No.: PCT/EP98/00816
  § 371 Date: Dec. 14, 1999
  § 102(e) Date: Dec. 14, 1999
(87) PCT Pub. No.: WO98/36735
  PCT Pub. Date: Aug. 27, 1998

(30) Foreign Application Priority Data

Feb. 20, 1997 (IT) .......................................... MI97A0363

(51) Int. Cl.$^7$ ................................................ A61K 9/127
(52) U.S. Cl. ...................................................... 424/450
(58) Field of Search ........................... 424/450; 264/4.1, 264/4.3, 4.6; 514/2, 8, 21, 885

(56) References Cited

FOREIGN PATENT DOCUMENTS

| DE | 4038075 | * | 3/1992 |
| EP | 05 78 620 | * | 1/1994 |
| WO | 86 00238 | * | 1/1986 |
| WO | 96/400064 | * | 12/1996 |

OTHER PUBLICATIONS

Pick in ABB. 212 # 1 pp 186–194, 1981.*

* cited by examiner

*Primary Examiner*—Gollamudi S. Kishore
(74) *Attorney, Agent, or Firm*—Oblon, Spivak, McClelland, Maier & Neustadt, P.C.

(57) ABSTRACT

Aqueous pharmaceutical composition comprising an active agent which is highly insoluble in water, dispersed in liposomes and method of preparation are disclosed.

15 Claims, No Drawings

AQUEOUS PHARMACEUTICAL COMPOSITION COMPRISING AN ACTIVE INGREDIENT WHICH IS HIGHLY INSOLUBLE IN WATER

This application is a 371 of PCT/EP98/00816 filed Feb. 12, 1998.

This invention relates to an aqueous pharmaceutical composition comprising an active ingredient which is highly insoluble in water. In particular, it relates to a pharmaceutical composition in which the active ingredient is dispersed in liposomes.

A great deal of research is being carried out to find new liposomal preparations in the pharmaceutical field. However, many difficulties have emerged particularly in relation to active ingredients which are highly insoluble in water. In particular, those with a solubility in water $\leq 0.01\%$ (w/v).

In fact, the technique currently used to produce liposomes comprising active ingredients of low water-solubility comprises:

a) solubilizing of the active ingredient and the preselected phospholipids in a suitable organic solvent, for example, chloroform;
b) evaporation of this solvent at reduced pressure to give an active ingredient/phospholipid film;
c) addition of a second organic solvent, for example, terbutylic alcohol;
d) freezing of the solution obtained at the temperature of liquid nitrogen;
e) lyophilisation of the frozen solution;
f) hydration of the lyophilised solution with a buffer solution to give a suspension of multilamellar liposomes (MLV); and
g) treatment of this suspension with ultrasound to give a suspension of smaller liposomes (SUV).

An example of this method is described by A. Sharma et al. "Pharmaceutical Research", 2 (6), 889–896 (1994).

This technique, however, has the disadvantage of being very laborious and leads to the presence of traces of organic solvents in the liposomes. sphingolipids and mixture thereof. More preferably, they are made up of phospholipids. A typical example of the liposomal composition according to this invention comprises phosphatidylcholine, lysophosphatidylcholine, N-acyl-phosphatidylcholine, phosphatidyl ethanolamine, phosphat-idylserine, sphingomyelin, non-polar lipids, triglycerides, free fatty acids, DL-α-tocopherol.

A preferred liposomal composition according to this invention comprises:

| Component | % (w/w) |
| --- | --- |
| phosphatidylcholine | 85–97 |
| lysophosphatidylcholine | 0–5 |
| N-acyl-ethanolamine | 0–4 |
| phosphatidyl ethanolamine | 0–10 |
| triglycerides | 0–4 |
| free fatty acids | 0–3 |
| DL-α-tocopherol | 0–1 |

A particularly preferred liposomal composition according to this invention comprises:

| Component | % (w/w) |
| --- | --- |
| phosphalidylcholine | 94 |
| lysophosphatidylcholine | 3 |
| N-acyl-ethanolamine | 1 |
| phosphatidyl ethanolamine | 0.1 |
| triglycerides | 1 |
| free fatty acids | 0.75 |
| DL-α-tocopherol | 0.15 |

Typically, the size of the liposomes according to this invention is less than 500 nm. Preferably, this is from 50–250 nm.

A second object of this invention is a method for the preparation of an aqueous pharmaceutical composition with an active ingredient which is highly insoluble in water, dispersed in liposomes, which is characterised by the fact that it comprises the following phases:

a) dispersion of this active ingredient in lipids at a temperature of between 20 and 30° C.;
b) suspension of this dispersion in an aqueous phase;
c) resting of this suspension at ambient temperature for a period of between 0 and 48 hours;
d) heating to 30–75° C. for 10–40 minutes;
e) freezing at −150/−200° C.;
f) repetition of phases d) and e) at least twice and not more than 8 times;
g) filtration through a filtering membrane with pores of diameter 500–1000 nm;
h) extrusion through a membrane with pores of diameter 50–400 nm; and at the same time
i) removal of any active ingredient which is not trapped.

The duration of phase c) depends on the quantity of active ingredient highly insoluble in water to be trapped in the liposomes. The person skilled in the art does not therefore encounter any difficulties since a few simple routine experiments will determine the correct time for each type of active ingredient and liposomal composition.

The aqueous phase shall preferably be made up of an aqueous solution of sodium chloride at 0.05% –0.9% (w/v).

Typically, the quantity of lipid used is between 0.01–0.4 parts by weight for each part by weight of aqueous solution. In turn, the quantity of active ingredient is typically between 0.01 and 0.3 parts by weight for each part by weight of lipid.

Typically, the disperser is a homogeniser of the Ultraturrax™ type.

Typically, the extrusion is carried out using compressed air or an inert gas, chosen from the group comprising nitrogen, helium and argon, as the extrusion gas. The preferred inert gas is helium. In the extrusion phase, the pressure shall preferably be between 500 and 5500 kPa and the temperature shall preferably be between 20 and 75° C., and even more preferably between 40 and 65° C. Typical examples of suitable extruders are those of the Lipex Biomembranes Thermobarrel type or of the Emulsiflex CC Avestin type with filters with polycarbonate Costarm membranes with pores of between 50 and 600 nm.

Typically phase h) is repeated at least twice and not more than 8 times. Preferably 6 times.

The following examples illustrate this invention without limiting it in any way.

EXAMPLE 1

100 mg of melatonin were dispersed in 1 g of phospholipid at 30° C. for 10 minutes using an Ultraturrax™ type homogeniser. Immediately afterwards, this dispersion was suspended in 10 ml of aqueous solution of sodium chloride at 0.9% (w/v) using the said homogeniser and then heated in a water bath at 55° C. for 20 minutes.

The suspension obtained in this way was subject to the following cycle of cooling and heating:
 cooling in liquid nitrogen for 1 minute,
 heating to 55° C. until the phospholipids are completely fluid.

This cycle was repeated 6 times.

The suspension was passed twice through a 0.6 pm filter with the Lipex Biomembrane apparatus.

Thus, a "Multilamellar Large Vesicles" (MLV) suspension was obtained which was subjected to 6 cycles of continuous extrusion using a 10 ml extruder of the Lipex Biomembranes Extruder Thermobarrel type with 0.1 $\mu$m polycarbonate Costar™ filters at 55° C., using helium, as the extrusion gas, at a pressure of between 1000 and 4800 kPa.

Operating as described above three batches of the product (LM/186, LM/188 and LM/190) were prepared.

The following tests were carried out on the batches:
 melatonin amount in the aqueous liposomal composition (HPLC analysis);
 liposome size;
 quantity of melatonin trapped in the liposomes.

The following table shows the parameters measured and their significance:

| Parameters | Significance |
|---|---|
| liposome size | stability in the formulation time; measurement of the "fusion" of the vesicles; |
| melatonin amount | concentration of melatonin in the aqueous liposomal composition; stability in the formulation time; |

The data obtained are given in Table 1 which shows:
 the concentration of melatonin obtained in the aqueous liposomal formulation was, expressed as an average value for the three batches, $8.05 \times 10^{-3}$ g/ml;
 the average size of the liposomes for the three batches was 93 nm;
 the quantity trapped, expressed as an average value for the three batches, was 80.5 $\gamma$/mg;
 the formulations showed no liposome aggregation phenomena.

TABLE 1

| batch | HPLC amount (mg/ml) | average size (nm) | quantity trapped ($\gamma$/mg)* |
|---|---|---|---|
| LM/186 | 7.8 | 85 | 78 |
| LM/188 | 8.46 | 97 | 84.6 |
| LM/190 | 7.9 | 98 | 79 |

*expressed as $\gamma$ of drug per mg of phospholipids used.

The following procedure was used for the HPLC analysis:
 fixed phase: column in inverse phase PKB-100 (250×4.6 mm; 5 $\mu$m Supelco);
 mobile phase: water:acetonitrile 80:20 (v/v);
 detection: UV 254 nm.

Two pieces of apparatus are used for the analysis of the average size of the liposomes:
 1) DELSA 440 Coulter,
 2) NICOMP Submicron particle sizer model 370.

The procedure was as follows:
 a) for the tests carried out with apparatus 1), 1 ml of liposomal suspension was diluted with 10 ml of aqueous solution of sodium chloride at 0.9% (w/v);
 b) for the tests carried out with apparatus 2), 0,5 ml of solution a) was diluted to 10 ml with aqueous solution of sodium chloride at 0.9% (w/v).

EXAMPLE 2

Proceed as described in Example 1 above, using 2 g of phospholipid and 50 mg of lonidamine in place of 1 g of phospholipid and 100 mg of melatonin.

Thus three batches of the product (LM/1 95, GN/1 L and GN/2L) are prepared. The data obtained are given in Table 2 which shows:
 the concentration of lonidamine in the aqueous composition went from the initial solubility value of $3 \times 10^{-6}$ g/ml to an average value for the three batches of $3.83 \times 10^{-3}$ g/ml;
 the average size of the liposomes for the three batches was 79.6 nm;
 the quantity trapped, expressed as an average value for the three batches, was 19.2$\gamma$/mg;
 the formulations showed no liposome aggregation phenomena.

TABLE 2

| batch | HPLC amount (mg/ml) | average size (nm) | quantity trapped ($\gamma$/mg)* |
|---|---|---|---|
| LM/195 | 3.66 | 103 | 18.3 |
| GN/1L | 3.31 | 53 | 16.5 |
| GN/2L | 4.54 | 76 | 22.7 |

*expressed as $\gamma$ of drug per mg of phospholipids used.

EXAMPLE 3

Proceed as described in Example 1 above, using 2 g of phospholipid and 200 mg of melatonin in place of 1 g of phospholipid and 100 mg of melatonin.

Thus three batches of the product (GN/1 M, GN/2M and GN/3M) were prepared. The data obtained are given in Table 3 which shows:
 the concentration of melatonin in the aqueous liposomal formulation, expressed as an average value for the three batches, was $13.5 \times 10^{-3}$ g/ml;
 the average size of the liposomes for the three batches was 92.6 nm;
 the quantity trapped, expressed as an average value for the three batches, was 67.6 $\gamma$/mg;
 the formulations showed no liposome aggregation phenomena.

TABLE 3

| batch | HPLC amount (mg/ml) | average size (nm) | quantity trapped (γ/mg)* |
|---|---|---|---|
| GN/1M | 10.66 | 104 | 53.3 |
| GN/2M | 13.90 | 76 | 69.5 |
| GN/3M | 16.03 | 98 | 80.15 |

*expressed as γ of drug per mg of phospholipids used.

EXAMPLE 4

Proceed as described in Example 2 above, except that the extrusion is carried out through a polycarbonate membrane of 0.2 μm rather than 0.1 μm.

Thus three batches of the product (GN/3L, GN/4L and GN/5L) were prepared.

The data obtained are given in Table 4 which shows that, by increasing the lonidamine from 20 mg to 50 mg, the quantity of phospholipid for 1 to 2 g and extruding with a 0.2 μm instead of a 0.1 μm membrane, a significant increase in the concentration of lonidamine in the aqueous composition was obtained in example 2. In fact, an average value of $4.47 \times 10^{-3}$ g/ml was obtained for the concentration of lonidamine.

TABLE 4

| batch | HPLC amount (mg/ml) | average size (nm) | quantity trapped (γ/mg)* |
|---|---|---|---|
| GN/3L | 4.23 | 134 | 21.15 |
| GN/4L | 4.44 | 129 | 22.20 |
| GN/5L | 4.75 | 109 | 23.75 |

*expressed as γ of drug per mg of phospholipids used.

EXAMPLE 5

20 mg of cyclosporin-A were dispersed in 1 g of phospholipid at 30° C. for 10 minutes using an Ultraturrax™ type homogeniser. Immediately afterwards, this dispersion was suspended in an aqueous solution of sodium chloride at 0.9% (w/v) using the said homogeniser and then heated in a water-bath at 65° C. for 20 minutes. The suspension obtained in this way was subject to the following cycle of cooling and heating:

cooling in liquid nitrogen for 1 minute, heating to 65° C. until the phospholipids are completely fluid.

This cycle was repeated 6 times.

The suspension was passed twice through a 0.6 μm filter with the Lipex Biomembrane apparatus.

Thus a "Multilamellar Large Vesicles" (MLV) suspension was obtained which was subjected to 6 cycles of continuous extrusion using a 10 ml extruder of the Lipex Biomembrane Extruder Thermobarrel type with 0.1 μm polycarbonate Costar™ filters at 65° C., using helium as the extrusion gas at a pressure of between 1000 and 4800 kPa.

Thus three batches of the product (LM/416A, LM/416B and LM/416C) were prepared.

The data obtained are given in Table 5 which shows:

the concentration of cyclosporin-A in the aqueous liposomal formulation, expressed as an average value for the three batches, was $0.96 \times 10^{-3}$ g/ml;

the average size of the iiposomes for the three batches was 103 nm;

the quantity trapped, expressed as an average value for the three batches, was 9.6γ/mg;

the formulations showed no liposome aggregation phenomena.

TABLE 5

| batch | HPLC amount (mg/ml) | average size (nm) | quantity trapped (γ/mg)* |
|---|---|---|---|
| LM/416A | 0.96 | 103 | 9.6 |
| LM/416B | 0.94 | 99 | 9.4 |
| LM/416C | 0.98 | 107 | 9.8 |

*expressed as γ of drug per mg of phospholipids used.

EXAMPLE 6

Proceed as described in Example 1 above, using 2 g of phospholipids and 50 mg of bindarit in place of 1 g of phospholipids and 100 mg of melatonin.

Thus three batches of the product (LM/356, LM/357 and LM/358) were prepared.

The data obtained are given in Table 6 which shows:

the concentration of bindarit in the aqueous liposomal composition went from the initial solubility value of $1 \times 10^{-4}$ g/ml to an average value for the three batches of 4 mg/ml;

the average size of the liposomes for the three batches was 108.3 nm;

the quantity trapped, expressed as an average value for the three batches, was 20.2 γ/mg;

TABLE 6

| batch | HPLC amount (mg/ml) | average size (nm) | quantity trapped (γ/mg)* |
|---|---|---|---|
| LM/356 | 4.1 | 109.4 | 20.5 |
| LM/357 | 4 | 109.7 | 20 |
| LM/358 | 4 | 106 | 20 |

*expressed as γ of drug per mg of phospholipids used.

the formulations showed no liposome aggregation phenomena.

EXAMPLE 7

30mg of cyclosporin-A were dispersed in 2 g of phospholipid at 30° C. for 10 minutes using an Ultraturrax™ type homogeniser. Immediately afterwards, this dispersion was suspended in an aqueous solution of sodium chloride at 0.9% (w/v) using the said homogeniser and left to rest at ambient temperature for 24 hours. Then the suspension obtained was heated in a water-bath at 65° C. for 20 minutes.

The suspension obtained in this way was subject to the following cycle of cooling and heating:

cooling in liquid nitrogen for 1 minute, heating to 65° C. until the phospholipids are completely fluid.

This cycle was repeated 6 times.

The suspension was passed twice through a 0.6 pm filter with the Lipex Biomembrane apparatus.

Thus, a "Multilamellar Large Vesicles" (MLV) suspension was obtained which was subjected to 6 cycles of continuous extrusion using an extruder of the 10 ml Lipex Biomembrane Extruder Thermobarrel type with 0.1 μm polycarbonate Costar™ filters at 65° C., using helium as the extrusion gas at a pressure of between 1000 and 4800 kPa.

Thus three batches of the product (LM/422a, LM/422b and LM/422c) were prepared.

The data obtained are given in Table 7 which shows:

the concentration of cyclosporin-A in the aqueous liposomal formulation, expressed as an average value for the three batches, was 3 mg/ml;

the average size of the liposomes for the three batches was 119.5 nm;

the quantity trapped, expressed as an average value for the three batches, was 15 γ/mg;

the formulations showed no liposome aggregation phenomena.

TABLE 7

| batch | HPLC amount (mg/ml) | average size (nm) | quantity trapped (γ/mg)* |
|---|---|---|---|
| LM/422a | 3.2 | 121.5 | 16 |
| LM/422b | 3 | 117.9 | 15 |
| LM/422c | 2.8 | 119 | 14 |

*expressed as γ of drug per mg of phospholipids used.

What is claimed is:

1. An aqueous pharmaceutical composition comprising an active ingredient having a solubility in water not higher than 0.01% dispersed in liposomes wherein said active ingredient is lonidamine or bindarit.

2. The composition according to claim 1, wherein the liposomes comprise a component selected from the group consisting of phosphoglycerides, mono-, di-, and tri-esters of glycerols, phospholipids, galactosyl and glucosyl lipids, cholesterol derivatives, sphingolipids and mixtures thereof.

3. The composition according to claim 1, wherein the liposomes comprise a composition comprising phosphatidylcholine, lysophosphatidylcholine, N-acyl-phosphatidylcholine, phosphatidyl ethanolamine, phosphatidylserine, sphingomyelin, triglycerides, free fatty acids, DL-α-tocopherol.

4. The composition according to claim 1, wherein the liposomes comprise non-polar lipids.

5. The composition according to claim 2, wherein the quantity of lipids is between 0.01 and 0.4 parts by weight for each party by weight of water.

6. The composition according to claim 2, wherein the quantity of the active ingredient is between 0.01 and 0.3 parts by weight for each part by weight of lipids.

7. A method for the preparation of an aqueous pharmaceutical composition with an active ingredient highly insoluble in water, dispersed in liposomes, which comprises the following phases:

a) dispersion of the active ingredient in lipids at a temperature of between 20 and 30° C.;

b) suspension of this dispersion in an aqueous phase;

c) resting of this suspension at ambient temperature for a period of between 0.1 and 48 hours;

d) heating to 30–75° C. for 10–40 minutes;

e) freezing at −150/−200° C.;

f) repetition of phases d) and e) at least twice and not more than 8 times;

g) filtration t hrough a filtering membrane with pores of diameter 500–1000 nm;

h) extrusion through a membrane with pores of diameter 50–400 nm; and at the same time i) removal of any active ingredient which is not trapped.

8. The method according to claim 7, wherein the aqueous phase comprises an aqueous solution of sodium chloride at 0.05%–0.9% (w/v).

9. The method according to claim 7, wherein the quantity of lipids used is between 0.01 and 0.4 parts by weight for each part by weight of water.

10. The method according to claim 7, wherein the quantity of the active ingredient used is between 0.01 and 0.3 parts by weight for each part by weight of lipids.

11. The method according to claim 7, wherein an extrusion gas selected from the group consisting of air, nitrogen, helium and argon is used in phase (h).

12. The method according to claim 11, wherein the extrusion gas has a pressure of between 500 a nd 5500 kPa.

13. The method according to claim 7, wherein phase h) is carried out at a temperature of between 20 and 75° C.

14. The method according to claim 13, wherein the temperature is between 40 and 65° C.

15. The method according to claim 7, wherein phase h) is repeated at least twice and not more than 8 times.

* * * * *